(12) United States Patent
Bertozzi et al.

(10) Patent No.: US 8,023,618 B2
(45) Date of Patent: Sep. 20, 2011

(54) METHODS AND APPARATUS FOR THE IDENTIFICATION OF MOLECULAR AND CRYSTALLINE MATERIALS BY THE DOPPLER BROADENING OF NUCLEAR STATES BOUND IN MOLECULES, CRYSTALS AND MIXTURES USING NUCLEAR RESONANCE FLUORESCENCE

(75) Inventors: William Bertozzi, Lexington, MA (US); Robert J. Ledoux, Harvard, MA (US)

(73) Assignee: Passport Systems, Inc., Billerica, MA (US)

( * ) Notice: Subject to any disclaimer, the term of this patent is extended or adjusted under 35 U.S.C. 154(b) by 107 days.

(21) Appl. No.: 12/333,505

(22) Filed: Dec. 12, 2008

(65) Prior Publication Data

US 2009/0213993 A1    Aug. 27, 2009

Related U.S. Application Data

(60) Provisional application No. 61/013,137, filed on Dec. 12, 2007.

(51) Int. Cl.
*G01N 23/201* (2006.01)
*G01N 23/22* (2006.01)

(52) U.S. Cl. ............................................ 378/86; 378/88

(58) Field of Classification Search .............. 378/44–46, 378/49, 70, 86, 88
See application file for complete search history.

(56) References Cited

U.S. PATENT DOCUMENTS

| | | | | |
|---|---|---|---|---|
| 5,040,200 | A * | 8/1991 | Ettinger et al. | 378/88 |
| 5,115,459 | A * | 5/1992 | Bertozzi | 378/88 |
| 5,293,414 | A * | 3/1994 | Ettinger et al. | 378/88 |
| 5,323,004 | A * | 6/1994 | Ettinger et al. | 250/336.1 |
| 5,420,905 | A * | 5/1995 | Bertozzi | 378/88 |
| 2006/0188060 | A1 * | 8/2006 | Bertozzi et al. | 378/57 |
| 2006/0193433 | A1 * | 8/2006 | Ledoux et al. | 378/57 |
| 2009/0147920 | A1 * | 6/2009 | Barty et al. | 378/88 |
| 2009/0196397 | A1 * | 8/2009 | Bertozzi et al. | 378/87 |

OTHER PUBLICATIONS

Moreh, et al. "Wdiths of 11B levels below 9.0 MeV", May 27, 1980, Physical Review C, vol. 22, No. 5, pp. 1820-1825.*
Palathingal, et al., "Nuclear Resonance Fluorescence and Rayleigh Scattering From 203 Tl", 1967, Nuclear Physics A101, pp. 193-201.*
Shvyd'Ko, et al., "Nuclear Resonant Scattering of Synchotron Radiation from 161-Dy at 25.61 keV", Oct. 15, 2001, Europhysics Letters, vol. 56, No. 2, pp. 309-315.*
Morse, et al., "Mechancial Doppler Compensation for Electron Excitation of NRF Photons", 2008, IEEE Science Symposium Conference Record, pp. 692-694.* Bertozzi, W. and Ledoux, R., *Nuclear resonance fluorescence imaging in non-intrusive cargo inspection,* Nucl. Instr. and Meth. in Phys. Res B 241, Aug. 30, 2005, 820-825; p. 823, col. 1, paragraph 1.
International Search Report and Written Opinion for PCT/US08/86524, (2008).

* cited by examiner

*Primary Examiner* — Anastasia Midkiff
(74) *Attorney, Agent, or Firm* — Foley Hoag LLP

(57) ABSTRACT

The broadening of the lines in NRF from an isotope that is part of a material may be due to several causes: the temperature of the material, the molecular structure of the material and the crystalline structure of the material. By measuring the broadening caused by the molecular structure and the crystalline structure the material itself can be identified. The exact energy of the lines in NRF may also depend on the nature of the crystalline and molecular structure of the material. By measuring the changes in the energy of the NRF lines caused by the structure of the material the material itself may be identified. These techniques provide a "fingerprint" of the molecule or crystal that is involved. The fingerprint information may be used to determine a potential threat.

48 Claims, 9 Drawing Sheets

METHODS AND APPARATUS FOR THE IDENTIFICATION OF MOLECULAR AND CRYSTALLINE MATERIALS BY THE DOPPLER BROADENING OF NUCLEAR STATES BOUND IN MOLECULES, CRYSTALS AND MIXTURES USING NUCLEAR RESONANCE FLUORESCENCE

CROSS-REFERENCE TO RELATED APPLICATION

This present application claims priority to and the benefit of U.S. Provisional Patent Application Ser. No. 61/013,137 entitled "A Method for the Identification of Molecular and Crystalline Materials by the Doppler Broadening of Nuclear States Bound in Molecules, Crystals and Mixtures Using Nuclear Resonance Fluorescence," which was filed on Dec. 12, 2007 by William Bertozzi and Robert J. Ledoux, and which is hereby incorporated by reference.

FIELD OF THE INVENTION

Nuclear Resonance Fluorescence (NRF) is used to determine the molecular and crystalline nature of substances via the broadening and shifting of the energies of intrinsic NRF lines.

BACKGROUND

Nuclear Resonance Fluorescence results when a nucleus is excited by photon absorption and then subsequently decays via photon emission to lower lying states of that nucleus. The decay is often but not always to the ground state. The emitted photon energy that results from a decay may be characteristic of the specific isotope which has decayed and therefore the detection of a photon of that energy may allow the identification of the presence of that isotope.

Because the emitted photon energies in NRF are in the MeV region, the photons involved may be very penetrating. This may allow NRF to be used for the non-intrusive inspection of dense cargo or materials. See U.S. Pat. No. 5,115,459, Explosives Detection Using Resonance Fluorescence of Bremsstrahlung Radiation, U.S. Pat. No. 5,420,905, Detection of Explosives and Other Materials Using Resonance Fluorescence, Resonance Absorption, and Other Electromagnetic Processes with Bremsstrahlung Radiation, and U.S. Pat. No. 7,120,226, Adaptive Scanning Of Materials Using Nuclear Resonance Fluorescence Imaging, the contents of all of which are hereby incorporated by reference.

The energies of the photons that are resonant with a specific isotope are for the most part determined by the nuclear structure of that isotope, and the nature of the strong nuclear interactions that bind that nucleus. Small effects may arise, however, from the recoil of the nuclear isotope due to the conservation of energy and momentum upon photon absorption and emission.

In particular, when a nuclear isotope absorbs a photon the energy of the absorbed resonant photon may not be simply the energy difference between the ground state of the nucleus and the resulting excited state of the nucleus. The photon energy must also account for the energy of excitation of the molecule or crystal to which the nucleus is bound. In a molecular structure, the molecule is generally excited because of the violent recoil of the nucleus caused by the conservation of momentum upon photon absorption. For light and heavy nuclei this recoil may be sufficient not just to excite the molecule but also to break the molecular bond. For crystalline materials, the recoil of the nuclear isotope may excite vibrations of the crystal in one or several of its many normal modes. The recoil may also break the nuclear isotope from its lattice position causing it to recoil almost freely through the crystal.

SUMMARY OF THE INVENTION

Nuclear Resonance Florescence (NRF) is used to determine the molecular and crystalline nature of a substance via the broadening and shifting of the energy of the intrinsic NRF lines. The broadening and shifting of the intrinsic NRF lines are different for each molecule or crystal due to the differences in the binding energies and details of the molecular or crystalline structure. Therefore, the molecular or crystalline configuration of a substance can be determined by NRF measurements which can determine the energy shift and/or the energy width of the broadened intrinsic NRF lines. This information about the molecular or crystalline configuration then can be used to differentiate between innocuous materials and dangerous materials or contraband that contains identical isotopes. For example, the major elemental constituents of high energy explosives (oxygen, carbon and nitrogen) are also found in common materials, but they have unique molecular configurations in the explosives. The method is non-intrusive because the energies of the NRF lines are in the MeV range and are very penetrating.

DETAILED DESCRIPTION OF THE PREFERRED EMBODIMENTS

The embodiments described herein illustrate applications of the technology disclosed for the identification of materials via Doppler broadening and energy shifts due to the specific nature of the molecular and crystalline structure of the materials (or lack thereof). Those experienced in the art will recognize that there are extensions, modifications and other arrangements of the important elements disclosed that can be implemented and they are included as part of this disclosure.

For a better understanding of the present disclosure, together with other and further objects thereof, reference is made to the accompanying drawings.

The processes described can be envisioned in a simple approximation that brings out the essentials of the processes. Let Q be the momentum of the photon, M the mass of the nuclear isotope and c the speed of light. (Vector quantities are bolded herein, amplitudes are not.) The isotope absorbs the photon of energy $E_0 = Qc$ and is excited to an energy E. Assuming the nucleus recoils freely having broken the bond of the crystal or molecule, one has the momentum and energy conservation equations, respectively:

$$Q + P_i = P_f \text{ (Momentum conservation)}$$

Figure 1:
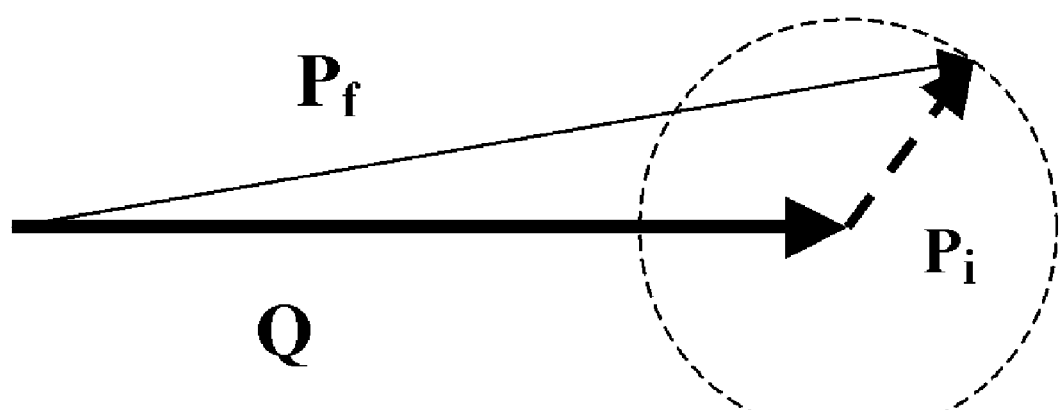
FIG. 1 shows the relationship between the momentum transfer Q, the initial momentum $P_i$, and the final momentum $P_f$ for an isotope interacting with an incident photon.

(See FIG. 1)

$$E_0 = E + (P_f)^2/2M + \epsilon \text{ (Energy conservation)}$$

In these expressions, the simplifying assumptions are made that the excited nucleus is recoiling freely, and that no other excitations of the remaining structures have occurred. The initial momentum of the nucleus bound to the molecule or atom is $P_i$; the final momentum of the recoiling nucleus is $P_f$, and the binding energy of the nucleus to the molecule or crystal lattice is $\epsilon$. (A non-relativistic approximation is adequate at these energies and momenta for the recoiling nucleus.)

These assumptions are reasonable. For example, in light nuclei an estimate of the recoil kinetic energy $E_r$ can be made by assuming that Q is the momentum of the nucleus after the collision, the nucleus is comprised of about 16 nucleons each of about 1 GeV mass, the nucleus is stationary before the collision, and the photon has energy of 4 MeV:

$$E_r = (1/2)(4)^2/(16 \times 10^9) = 500 \text{eV}.$$

That is, the nucleus has a recoil energy $E_r$ of approximately 500 eV, much more than any molecular or crystal binding energy. Thus, the recoil nucleus is moving rapidly compared to the molecular motions, justifying the above assumptions. In heavy nuclei with A ~200 this recoil energy $E_r$ is of the order of 40 eV, the energy of recoil remains larger than molecular or crystalline binding, and the above approximations, while not as precise, still embody the essential physics of the processes.

In reality, the initial momentum, $P_i$, of the nucleus is distributed in momentum space. Its probability amplitude may be derived from the Fourier decomposition of the wave function of the nucleus in the ground state of the molecule or crystal. This approximation does not incorporate the complexities of the distortion of the final state wave function by the molecular and crystalline interactions. However, it embodies the essential physics. These motions in the initial state are often referred to as "zero point motion" of the nucleus in the molecule or the crystal.

A more refined examination of the photon energy $E_0$ taking into account the initial nuclear momentum using energy conservation yields:

$$E_0 = E + (Q^2)/2M + (P_i)^2/2M - 2QP_i \cos(\theta_{QPi})/2M + \epsilon$$

$\theta_{QPi}$ is the angle between Q and $P_i$; for unpolarized molecules $\theta_{QPi}$ is randomly distributed. In the case of aligned or polarized molecules and crystals the distribution in $\theta_{QPi}$ is peaked accordingly. All the terms are of constant value except those involving $P_i$. For wave functions of about 1 angstrom dimensions, the approximate size of molecules, the term $(P_i)_2/2M$ is roughly 1/300 eV for nuclei in the region of mass number 25. It is dominated by the term $2QP_i \cos(\theta_{QPi})/2M$ which is of order 3 eV.

The term $2QP_i \cos(\theta_{QPi})/2M$ produces a broadening of an NRF line over a region of about ±3 eV in the case mentioned here. The distribution depends on the nature of the distribution of $P_i$. Sometimes it is called "Doppler Broadening" in the literature because it can be traced to the shift in wavelength of light emitted from or absorbed by a moving nucleus or photon source. The detail of the NRF broadening by the zero point motion is a property of the molecule since it is determined by the distribution of initial momentum, $P_i$. Both the distributions in amplitude and in direction of $P_i$ are important.

The binding energy parameter, $\epsilon$, is also of interest because it is different for different molecules and crystals and different environments of a molecule. It produces an energy shift that can also be detected by the methods discussed herein.

This discussion follows in the same way when one considers a monatomic atom. In this case there is no molecule or crystal to refer the nucleus to for its confinement and thus determine a distribution of $P_i$. However, there is a distribution of initial momenta characterized by the temperature of the monatomic gas. The term $2QP_i \cos(\theta_{QPi})/2M$ still dominates the broadening at room temperature except now the distribution of momentum is given by the standard Maxwellian distribution of velocities in a gas. Because of this feature the NRF broadening has been often called "thermal broadening" and "thermal Doppler broadening."

In the case of molecules and crystals the thermal effects are present just as with a monatomic gas; they are superimposed on the dynamical effects of the binding of the nuclear isotope to the molecule or crystal. In this case the apparent initial momentum distribution, $P_i$, has contributions from the thermal motion as well as from the effect of the binding of the molecule or crystal. This gives rise to differing treatments of the phenomenon, but the main effect remains: the characteristic broadening of the NRF lines remains intact and this broadening is a signature of the specific molecule and crystal.

Lamb provided an early treatment of the effects of binding and thermal motion on the apparent width of a resonance, for the case of neutron resonant scattering from crystals. (See "*Capture of Neutrons by Atoms in a Crystal*", Willis E. Lamb, Jr. Physical Review, 55, page 190, 1939). The treatment applies to photons as well. (See "*Resonance Fluorescence In Nuclei*", Franz R. Metzger, Progress In Nuclear Physics, 7, page 54, (1959) ("Metzger") and references therein). Lamb assumed that the crystal could be treated as a Debye continuum and that the binding of the lattice is weak so that $(\Delta + \Gamma) \gg 2k\theta$, where $\theta$ is the Debye temperature, $\Gamma$ is the natural width of the nuclear excitation, k is the Boltzmann constant and $\Delta$ is the thermal Doppler width of the resonance based on the actual temperature of the material, $\Delta = (E/c)(2kT/M)^{0.5}$. As an example, using E ~4 MeV and kT ~1/40 eV at room temperature, one arrives at $\Delta$ ~7 eV for a mass 16 nucleus and $\Delta$ ~2 eV for a mass 200 nucleus. Thus, the conditions proposed by Lamb are met since $2k\theta < \sim 1/5$ eV. Lamb showed that the Doppler width expression could be used in evaluating the broadening of a resonance in a crystal, with the temperature replaced by an effective temperature $T_{eff}$.

Figure 2:
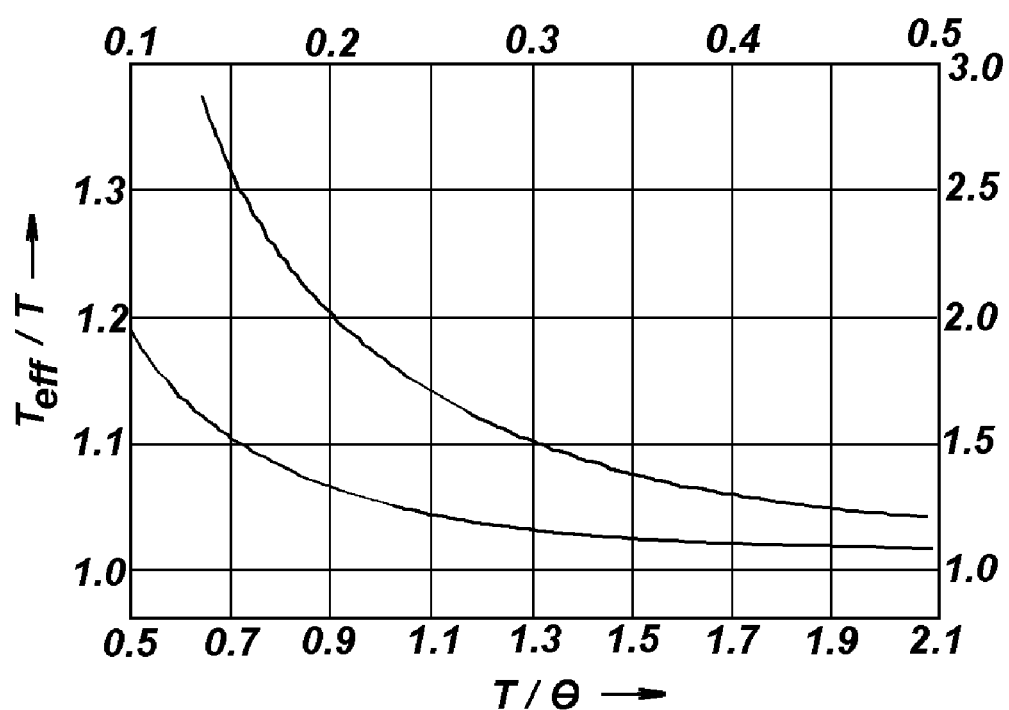
FIG. 2 shows the effect of crystalline binding on the temperature used in the calculation of $\Delta$, the Doppler width.

FIG. 2 shows the effect of crystalline binding. T is the actual temperature of the crystal, $\theta$ is the Debye temperature and $T_{eff}$ is the temperature used in the calculation of $\Delta$, the Doppler width. (The scales to the right and top apply to the upper curve. Those to the left and bottom apply to the bottom curve.) The relationship between $T_{eff}$ and the actual temperature, T, is shown in FIG. 2 where it is also assumed that a single Debye temperature describes the properties of the crystal. (FIG. 2 is from "*Resonance Fluorescence In Nuclei*", Franz R. Metzger, Progress In Nuclear Physics, 7, page 54, 1959)) According to FIG. 2, as the ratio $T/\theta$ increases, and particularly as T exceeds $\theta$, the ratio $T_{eff}/T$ decreases towards 1.

An evaluation of the cross section for excitation of an NRF state must incorporate the broadening effects discussed above by a convolution of the natural cross section for an isolated nucleus and the effects of the Doppler shifts. This results in the following expression ("*Resonance Fluorescence In Nuclei*", Franz R. Metzger, Progress In Nuclear Physics, 7, page 54, (1959)).

$$\sigma(E, t) = \int \sigma^0(E')w(E')dE' = \sigma^0_{max}\psi(x, t)$$

with $x = 2(E - E_r)/\Gamma$; $t = (\Delta/\Gamma)^2$ $$\psi(x, t) = \left[\frac{1}{2(\pi t)^{1/2}}\right]\int_{-\infty}^{\infty}\frac{\exp[-(x-y)^2/4t]}{1+y^2}dy$$

$$y = 2(E' - E_r)/\Gamma$$

Here, $\sigma^0_{max} = 4\pi\bar{\lambda}^2(2J_1+1)/2(2J_0+1)$, $\sigma^0_{max}$ is the maximum value of the cross section when it is not Doppler broadened. $\bar{\lambda}$ is the photon wavelength, $E_r$ is the resonance energy, $\Delta$ and $\Gamma$ are as defined earlier, and $J_0$ and $J_1$ are the angular momenta of the ground state and the excited states, respectively.

The integrated cross section of a resonance is a constant that is invariant to Doppler broadening. Because the cross section is distributed more broadly in energy as a result of the broadening, the maximum of the cross section is reduced. The broadening can be determined by measuring the maximum value of the broadened cross section and referring to the maximum value of the un-broadened cross section. One can also refer to the integrated cross section and its relation to the natural width by the relation:

Integrated cross section=$\sigma^0_{max}(\pi\Gamma/2)$.

Figure 3:
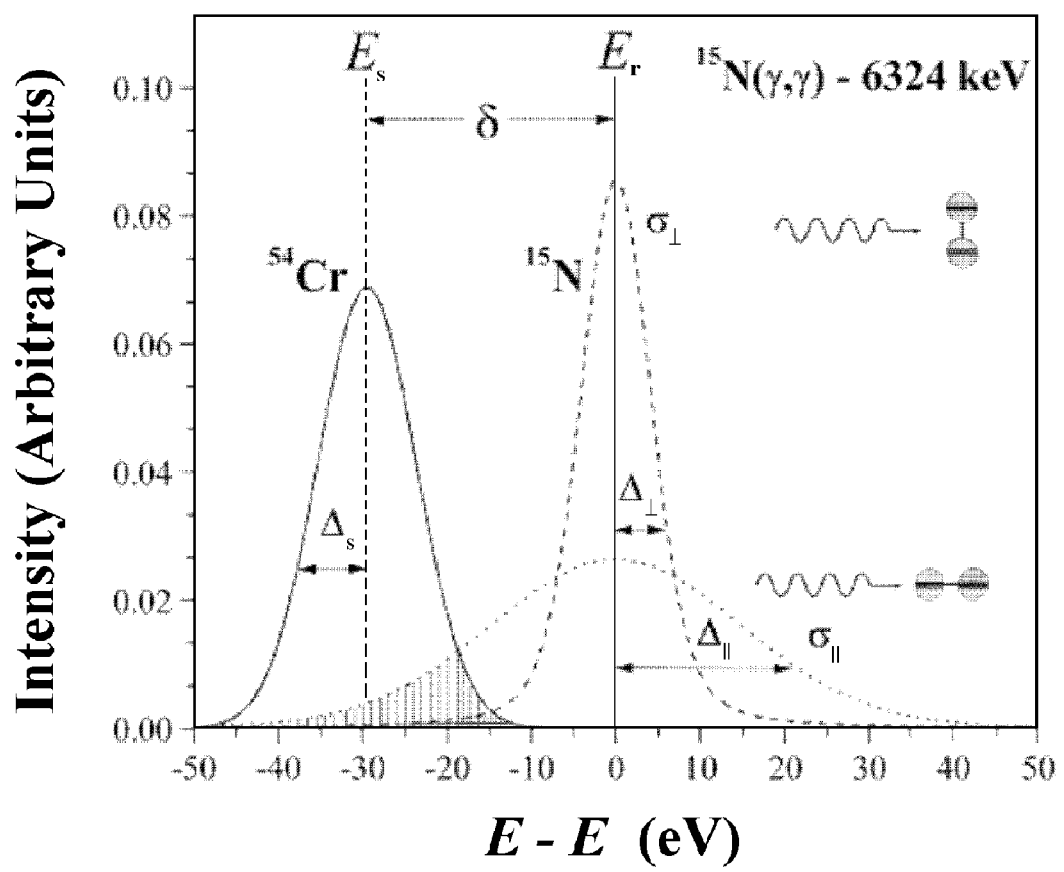
FIG. 3 shows the calculated shapes of the $^{53}Cr(n,\gamma)$ reaction line, and of the Doppler-broadened levels at 6324 keV in $^{15}N$, for incident photons parallel and perpendicular to the $N_2$ molecular axis, for Ts=460 K.

The Doppler broadening of nuclear levels caused by the zero-point vibrations and thermal motion has been used to measure the zero-point kinetic energies and momenta of atoms in solids and of molecules adsorbed on surfaces (see "*Nuclear Resonance Photon Scattering Studies of $N_2$ Adsorbed on Grafoil and of $NaNO_2$ Single Crystals*", R. Moreh, Y. Finkelstein and D. Nemirovsky, Journal of Research of the National Institute of Standards and Technology, 105, 159 (2000) ("Moreh et al.") and references therein.). These authors used the monochromatic photons from the $^{54}Cr(n,\gamma)$ reaction (the neutrons are from a reactor), which lies 29.5 eV below the energy of the 6324 keV level in $^{15}N$, to study NRF scattering for various configurations of the $N_2$ molecule. The broadened lines and levels are shown in FIG. 3, which is from Moreh et al. These results illustrate most of the physical principles and effects discussed herein.

Moreh et al. use the Doppler broadening of the nuclear level in $^{15}N$ caused not only by the thermal motion but also by the internal zero-point vibrational motion of the N-atom in the molecule. The overlapping process is such that the resonance scattering cross section is proportional to the Doppler broadening of the nuclear level, $$\Delta r = E(2kT_r/M_r c^2)^{1/2},$$

E is the excitation energy, $M_r$, the nuclear mass, $T_r$, the effective temperature of the scattering atom, k, the Boltzmann constant, and c the velocity of light.

Figure 5:
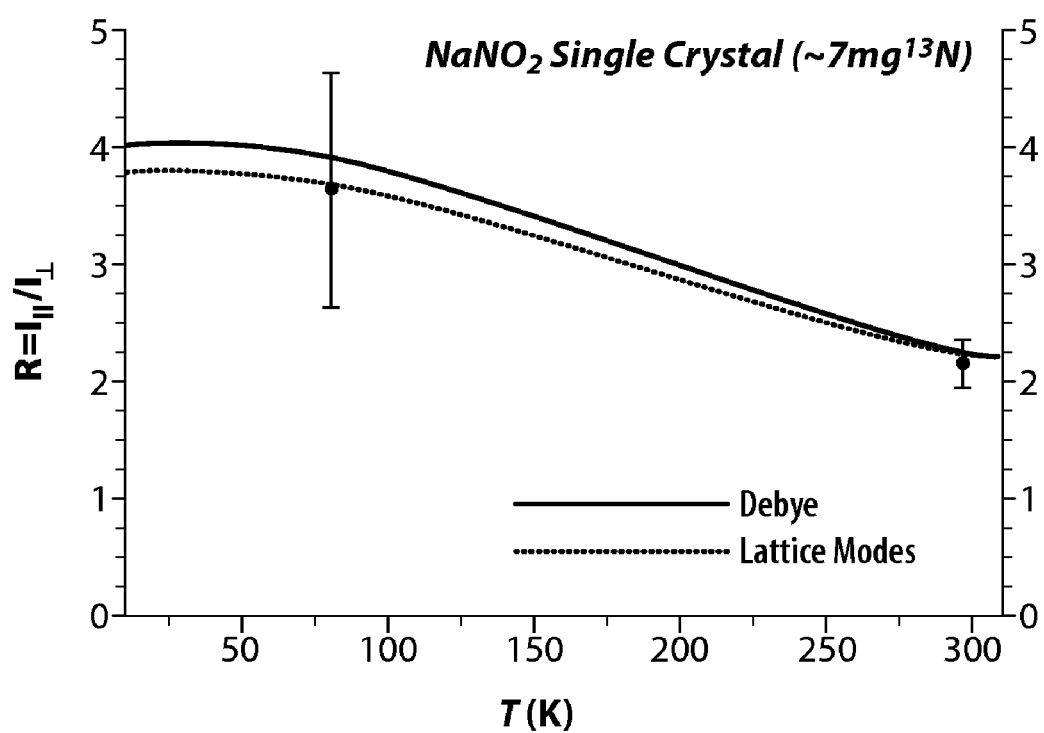
FIG. 5 shows measured scattered intensity ratios, $R=I_\parallel/I_\perp$ at 80K and 297 K with the photon beam parallel and perpendicular to the nitrite planes of the single crystal.

It may be noted that $T_r$ expresses the total kinetic energy of the scattering atom, including the part associated with its internal zero-point vibrational motion. This situation is schematically illustrated in FIG. 3 for the parallel and perpendicular orientations of the $N_2$ molecular axis with respect to the $\gamma$-beam direction. The diatomic $N_2$ molecule is highly anisotropic; the total kinetic energy of the N atom is at a maximum along the $N_2$ molecular axis (containing the internal vibrational motion) and at a minimum in the perpendicular direction. Hence the Doppler broadening of the $^{15}N$ nuclear level should have a maximum, $\Delta_{\|}$, along the $N_2$ symmetry axis and a minimum, $\Delta_{\perp}$, along the perpendicular direction. For incident photons from the $^{54}Cr(n,\gamma)$ reaction discussed above, the corresponding scattering cross sections $\sigma_{\|}$ and $\sigma_{\perp}$ yield respective scattering intensities $I_{\|}$ and $I_{\perp}$ that are proportional to the overlap integrals between the photons from the $^{54}Cr(n,\gamma)$ reaction and the broadened $^{15}N$ nuclear levels, and fulfill the relation $I_{\|} \gg I_{\perp}$. The ratio $R = I_{\|}/I_{\perp}$ is shown in FIG. 5 for $NaNO_2$.

Moreh et al. utilize this dependence of the scattering cross section on the orientation of $N_2$ with respect to the photon beam, in order to measure the out-of-plane tilt angle of the $N_2$ molecular axis with respect to the adsorbing graphite planes on the surface of graphite in the form of Grafoil on which $N_2$ monolayers are adsorbed. Based on the strong asymmetry in the NRF for photons from the $^{53}Cr(n,\gamma)$ reaction incident parallel to the surface compared to those incident perpendicular to the surface, they were able to establish the unique result that the molecular axis of $N_2$ adsorbed on Grafoil is oriented at approximately 7 degrees to the surface of the graphite.

Moreh et al. also illustrates the intimate relationship between the Doppler broadening of an NRF state and the symmetries and structure of a molecule in the case of $NaNO_2$, which is a molecular solid. The nitrite ions ($NO_2^-$) in a single crystal are all parallel to each other. $NaNO_2$ has nine vibrational modes (See "*Analysis of the Temperature Dependent Phonon Structure in Sodium Nitrite by Raman Spectroscopy*", C. Hartwig, E. Wiener Evnear, and S. P. S. Porto, Physical Review B 5, 79 (1972) ("Hartwig et al.")): three internal modes (825 cm−1<v<1321 cm−1) confined to the $NO_2$ ionic plane (FIG. 4), and six external modes of the lattice (of $Na^+$ against $NO_2^-$) which occur in the 120 $cm^{-1}$ to 220 $cm^{-1}$ spectral region. The internal modes (which are all planar) are the main contributors to the zero-point motion, making the single crystal highly anisotropic.

Figure 4:
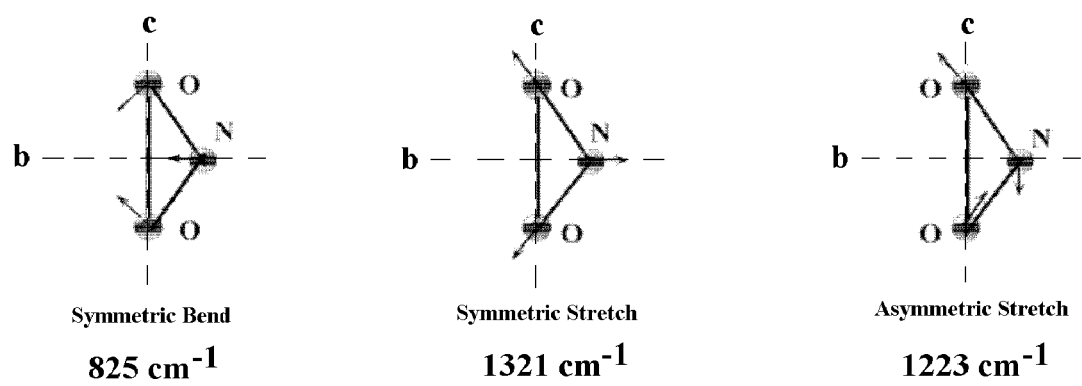
FIG. 4 shows the internal normal modes of $NO_2$.

FIG. 4 shows the internal normal modes of $NO_2$. (Vectorial arrows represent atomic motions.) Note that all modes are confined to the $NO_2^-$ plane (b,c). (FIG. 4 is from Moreh et al.) (taken from Hartwig et al.).

Some of the results of the work of Moreh et al are illustrated in FIG. 5, which. shows measured scattered intensity ratios, $R = I_{\|}/I_{\perp}$ at 80 K and 297 K with the photon beam parallel and perpendicular to the nitrite planes of the single crystal. The solid and dotted curves correspond to calculations using Debye and lattice modes. At 80K a very large anisotropy is observed, caused by the anisotropy in the zero-point motion of the internal modes of the $NO_2$ ion. This anisotropy, R, is approximately 3.6. (Taken from "*Nuclear Resonance Photon Scattering Studies of N2 Adsorbed on Grafoil and of NaNo2 Single Crystals*", R. Moreh, Y. Finkelstein and D. Nemirovsky, Journal of Research of the National Institute of Standards and Technology, 105, 159 (2000))

The results set forth above, along with other results of those authors and others, demonstrate that the specific characteristics of molecules, ions and crystals play a very important role in determining the Doppler broadening or energy shifts in the NRF process, and the resulting strength of the scattering and absorption processes. Conversely, the NRF process is capable of determining the Doppler broadening and energy shifts under varying conditions, and this broadening is an indicator of the specific nature of the molecule or crystal. This inverse process used to non-intrusively examine materials is the subject of this disclosure.

Figure 6:
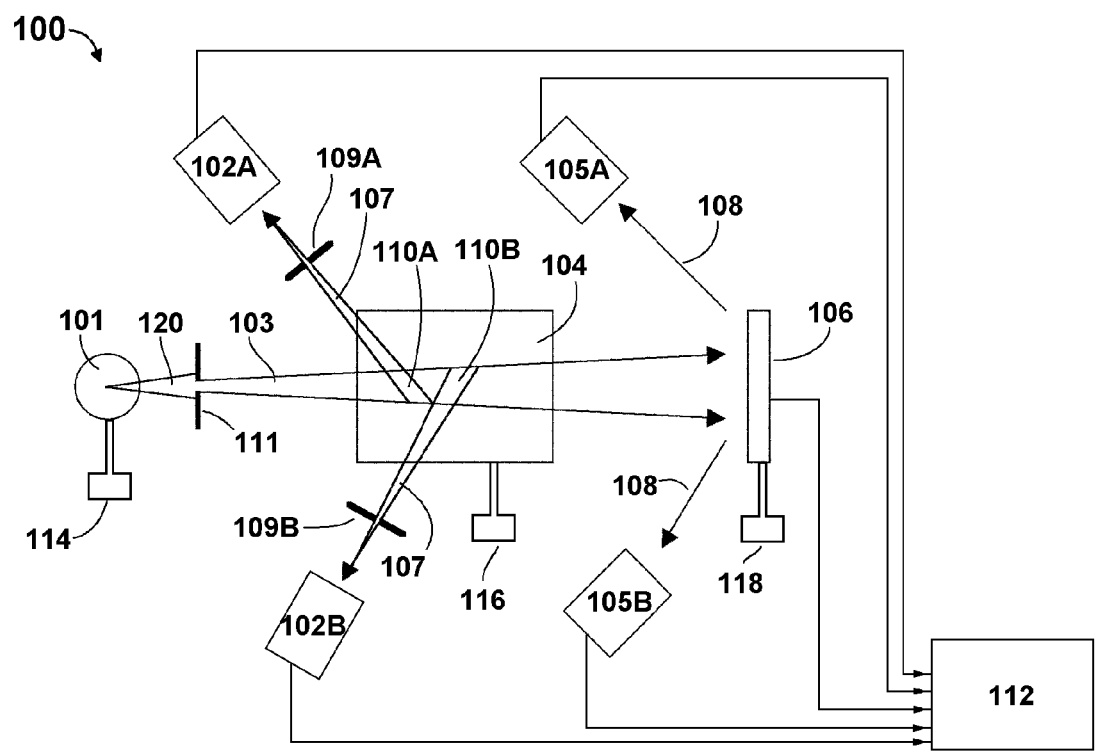
FIG. 6 shows generalized embodiments of apparatus for the detection processes described herein.

FIG. 6 is a schematic diagram 100 of possible embodiments of apparatus that may implement the methods described herein. (Of course, the methods may also be implemented by apparatus not illustrated in FIG. 6; that figure is by way of illustration and not limitation.) A photon source 101 may provide photons 120 that may be collimated by a collimator 111 to form a photon beam 103 that may impinge on a target 104. The target 104 may include material to be identified by NRF and for which it is also desired to determine information about the molecular and/or crystalline structure. Some of the photons in the photon beam 103 may scatter from the material in the target 104 and may impinge as scattered photons 107 on one or more detectors 102A, 102B, etc. The detectors 102A, 102B, etc. may be collimated by collimators 109A, 109B, etc. so as to view only a portion of the target 104 illuminated by the photon beam 103.

The intersection of the photon beam 103 and the collimated view of the target 104 from the detectors 102A, 102B define one or more "voxels" 110A, 110B, etc. within the target 104 that is being interrogated.

Some of the photon beam 103 may be transmitted through the target 104 and may interact with a reference target 106. The reference target 106 may but need not itself be a photon detector. The reference target 106 may comprise material related in a predetermined way to material in the target 104 or to material whose possible presence in target 104 may be of interest. The reference target 106 may comprise material related in a predetermined way to the specific nature of the photon source 101. The photons that impinge on the reference target 106 may be scattered and form scattered photons 108 which may be detected in one or more detectors 105A, 105B, etc. The detectors 105A, 105B, etc. may be collimated by collimators (not shown) so as to view only a portion of the reference target 106 illuminated by the photon beam 103 that has been transmitted through the target 104. The intersection of the photon beam 103 and the collimated view of the reference target 106 from the detectors 105A, 105B define one or more "voxels" (not shown) within the reference target 106.

The detectors 102A, 102B, etc. and/or 105A, 105B, etc. may be sensitive to the photon energy and be capable of recording and transmitting signals to analysis means 112 that may record and analyze the nature of the signals according to algorithms developed for the purpose of identification of the material in the target 104. The analysis means 112 may be a computer, microprocessor system, or other purpose-built system. By analyzing the nature of the signals it receives, according to the principles disclosed herein, the analysis means may determine the presence of certain isotopes and the nature of the molecules and/or crystalline structures in which the determined isotopes are incorporated. The analysis of the nature of the signals may include the identification of isotopes by detection of NRF lines and may further include the measurement of Doppler broadening of NRF lines and their energy shifts to determine the nature of the molecules and/or crystalline structures in which the NRF signals originated.

The photons 120 in the photon beam 103 may be continuously distributed in energy such as from bremsstrahlung or may be limited to a range in energy originating from processes such a nuclear reaction, Compton scattering, or laser backscattering from an electron beam. See U.S. Pat. No. 7,409,042, "Use Of Nearly Monochromatic And Tunable Photon Sources With Nuclear Resonance Fluorescence In Non-Intrusive Inspection Of Containers For Material Detection And Imaging," which is hereby incorporated herein by reference. If photon sources 101 containing several discrete photon "lines" are used, only one or a few of the lines may be used in these embodiments. Those skilled in the art will recognize that there are many possibilities for the photon source 101 and they are all included in this disclosure as possibilities.

Figure 7:
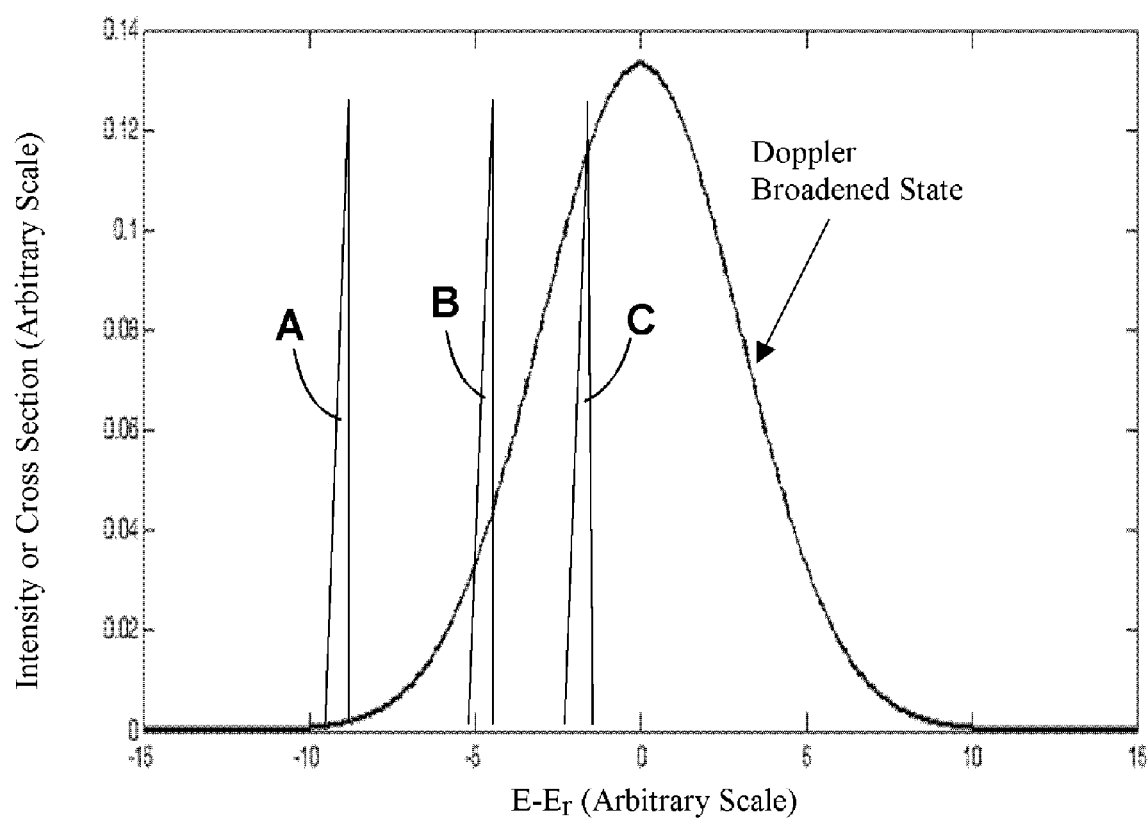
FIG. 7 shows a series of monochromatic photon lines placed at different energies to sample the scattering cross section of a Doppler-broadened state, or the attenuation caused by a Doppler-broadened state of some material.

In one embodiment the intensity of photons 107 scattered from the target 104 into the detectors 102A, 102B, etc. is measured as a function of the energy of the incident photons 103. This directly determines the Doppler broadening width of the material in the target 104 from which the scattering has taken place. An example of this technique is shown in FIG. 7. The cross section (vertical scale) of the Doppler-broadened state of the material in the target 104 from which the scattering has taken place is mapped as a function of $E-E_r$ (horizontal scale) where E is the incident photon 103 energy and $E_r$ is the resonance energy of the material in the target 104. Also shown is the intensity as a function of $E-E_r$ of three "monochromatic" incident photon 103 lines (A, B, and C), whose width in this example is smaller than the Doppler broadened NRF state, demonstrating the different amounts of overlap of the incident photons 103 from the photon source 101 and the cross section of the Doppler-broadened NRF state of the material in the target 104. Clearly, the number of photons interacting with and scattering through the NRF state of the material in the target 104 is largest in the "monochromatic" incident photon 103 line case C. By comparing the scattering intensity from the NRF state using incident photon 103 sources with suitably selected energies A, B and C, the Doppler broadened width of the NRF state of the material in the target 104 can be determined. Of course, the resonance energy $E_r$ and thus the nature of the material also may be determined.

Also, from FIG. 7 it can be seen that the absorption of the incident photons 103 by a target 104 with the Doppler broadened state will increase as the energy of the incident monochromatic photons 103 is varied from A to B to C. The transmission and resonant absorption of the monochromatic photon lines may be measured by the NRF transmission detector formed by reference target 106 (FIG. 6) and photon detectors 105A, 105B, etc. (FIG. 6) for measuring scattered photons 108 (FIG. 6). This transmission measurement also may map out the broadening of the NRF states of the selected isotopes that are incorporated into the reference target 106 (FIG. 6). In this embodiment and in other situations as will be recognized by those skilled in the art, reference target 106 of FIG. 6 may be simply a photon detector. When reference target 106 is simply a photon detector, it may be sensitive to the photon energy and be capable of recording and transmitting signals to analysis means 112.

Referring again to FIG. 7, it should be noted that the width of the monochromatic incident photon 103 lines need not be very narrow compared to the Doppler-broadened state of the material in the target 104 as depicted. If the energy width of each monochromatic photon source 101 is known then the overlap of the cross section of the Doppler-broadened state with the distribution in energy of the photon source 101 can be parameterized in terms of the widths of the state and of the energy widths of the photon sources. Thus, the resulting scattered intensity into detector 102A, 102B, etc. (FIG. 6) or the transmitted intensity as measured using reference target 106 can be used to determine the width of the Doppler-broadened state of the material in the target 104. Using two or more monochromatic lines that have different overlaps with the NRF state facilitates this determination.

Figure 8:
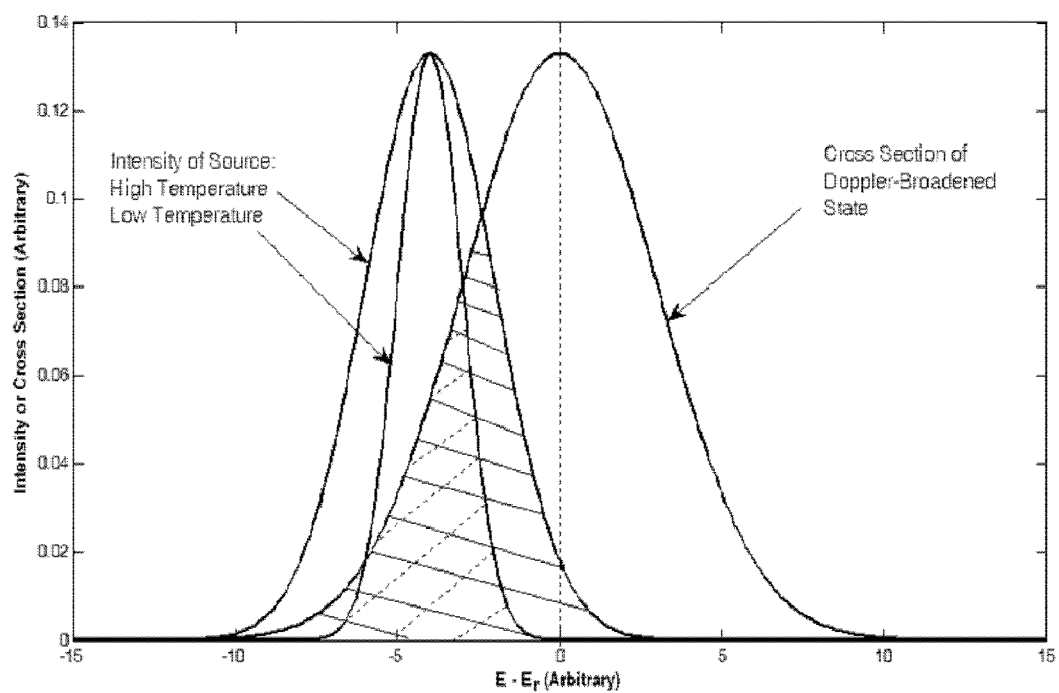
FIG. 8 shows how a source of photons may be broadened by changing its temperature.

Referring again to FIG. 6, in another embodiment, the energy width of the incident monochromatic photon beam 103 is varied by varying the temperature of the photon source 101. This changes the Doppler width of the photon source 101 and changes in a controlled manner the overlap in photon energy between the photon source 101 and the Doppler-broadened NRF states in the target 104 as illustrated in FIG. 8. Still referring to FIG. 6, the overlap of the intensity distribution of the photon source 101 with the cross section of the Doppler-broadened state in the target 104 can be parameterized in terms of the widths of these distributions. The overlap may be proportional to the scattered intensity detected by detectors 102A, 102B, etc. or the transmitted intensity detected by use of the reference target 106 (FIG. 6) and/or the photon detectors 105A, 105B, etc. for measuring scattered photons 108. From this temperature dependence of the energy width of the source photons 101, the Doppler width of the nuclear state in the target 104 may be determined. In this embodiment and in other situations as will be recognized by those skilled in the art, reference target 106 may be simply a photon detector.

FIG. 8 shows how a source of photons may be broadened by changing its temperature. Two such temperatures are shown, displaying the resulting different energy regions of overlap of the photon source 101 with the cross section of the Doppler-broadened state in the target 104. The angled dashed lines show the overlap with the low temperature distribution and the angled solid lines show the overlap with the high temperature distribution.

Once again referring to FIG. 6, in still another embodiment, the target 104 temperature may be changed to modify the Doppler width of the material in the target and thus the overlap with the energy of the incident beam 103. This can be illustrated by simply reversing the roles of the photon source 101 and the Doppler-broadened cross section of the material in the target 104 in FIG. 8. The contribution to the Doppler width made by the temperature will combine with the contributions to the broadening caused by molecular and crystalline structure, and measurements of the broadening at different temperatures will allow a separation of the molecular effects from the temperature effects. The scattered intensity detected by the one or more detectors 102A, 102B, etc. and the transmitted intensity detected by reference target 106 (FIG. 6) and/or photon detectors 105A, 105B, etc. for measuring scattered photons 108, will depend on the overlap of the photon intensity and cross section of the nuclear excitation and the Doppler broadening of the target 104 is thus determined. In this embodiment and in other situations as will be recognized by those skilled in the art, reference target 106 may be simply a photon detector.

Again referring to FIG. 6, in yet another embodiment the photon source 101 is moved by a motion actuator 114 so that the velocity of the photon source 101 varies so as to shift the energy of the photons in photon beam 103 from the photon source 101 directed to the target 104. The photon energy is shifted according to the well known Doppler shift:

$$\delta = \pm (v/c)E$$

where + pertains when the photon is emitted opposite to the direction of motion of the source and − pertains when the photon is emitted in the same direction as the direction of motion of the source. This technique provides a means of shifting the photon energy in a controlled manner. Referring to FIG. 7, shifting the monochromatic photon energy in a controlled manner may be used to provide the equivalent of monochromatic photon lines A, B and C.

In another embodiment, the target 104 is moved by a motion actuator 116 so that the resonant energy of the photon line is shifted according to the well known Doppler shift, in analogy with having the photon source 101 moved by a motion actuator. Referring to FIG. 7, shifting the resonant energy in a controlled manner may be used to provide the equivalent of monochromatic photon lines A, B and C.

In another embodiment, the reference target 106 may be moved by a motion actuator 118 so that its velocity will change the energy of NRF state of the reference target 106 via the well known Doppler shift. The scattered photons 108 from the reference target 106 detected by the one or more detectors 105A, 105B, etc. thus monitor the energy dependence of the absorption of the target 104 as it overlaps with the spectrum of the photon source 101. This dependence of the scattering probability from the reference target 106 as a function of the Doppler shift of the energy of the reference target 106 determines the energy dependence of the shape of the photon absorption through the target 104 as it overlaps with the photon source 101 and thus determines the Doppler width of the target 104. When a reference target 106 is used, its motion may be synchronized with the motion of the photon source 110 to maintain the appropriate relationship.

In the embodiments described above with motion actuators, the motion actuators may be, for example, linear actuators which may be reciprocating, or may be oscillatory actuators as for example rotating tables. A rotating table or linear motion actuator are exemplary of various techniques used to provide a velocity to a material and those skilled in the art will know of other means that can provide a velocity and these are included as part of this disclosure. The means of extracting the Doppler broadened widths by varying the velocity of photon source 101, target 104 or reference target 106 is in direct analogy to the discussions above in regards to changing the energy of a monochromatic photon source.

In another embodiment the reference target 106 is used to measure the attenuation of photons 103 from the photon source 101 by the target 104. This is achieved by resonantly scattering these photons by the reference target 106 into the one or more detectors 105A, 105B, etc. The attenuation of the target 104 depends on the peak of the NRF cross section and the amount of material in the target 104 that is along the path of the photon beam 103. Thus, the attenuation provides a measure of the Doppler broadening of the resonance state of the material in the target 104 because the peak NRF cross section depends on the Doppler broadening.

Using a monochromatic photon source 101 makes this embodiment effective with simply a photon detector as reference target 106. This application is illustrated in FIG. 7 which shows how monochromatic photon source lines can be scanned across the NRF state at different energies.

If a source distributed in energy is used then the signal in a photon detector employed as reference target 106 may have interference from photons not in the region of the resonance and the advantage lies with reference target 106 being a resonant reference scatterer and the scattered photons 108 being detected by the one or more detectors 105A, 105B, etc.

Figure 9:
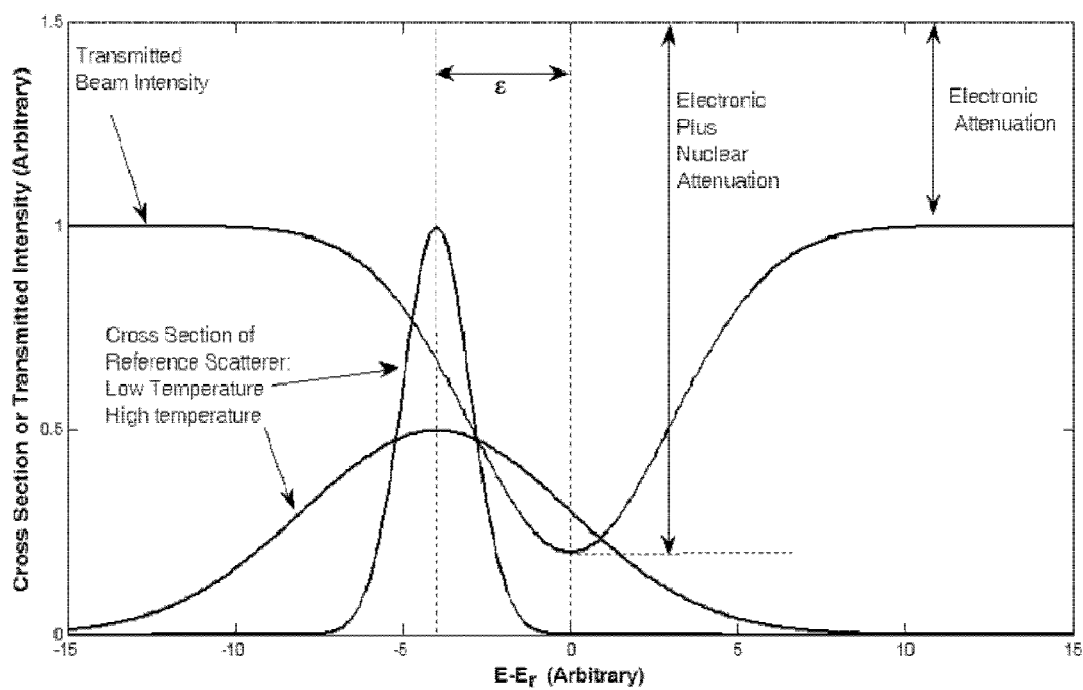
FIG. 9 shows the spectrum of photons transmitted through a material wherein the absorption includes the influence of a nuclear resonance, and it also demonstrates the different overlaps with an NRF state of a reference scatterer at two different temperatures.

Some of these concepts are illustrated in FIG. 9, which shows transmitted beam intensity from a photon source (corresponding to photon source 101 of FIG. 6) that is broad in energy. It could be a bremsstrahlung source as well as other types. The beam 103 transmitted through the target 104 suffers electronic attenuation in the region outside the resonance energy region of the material in the target 104. In the energy region of the target resonance the photon beam suffers both electronic and nuclear absorption as shown in FIG. 9. The reference target 106 is shown with a resonance energy different from that of the target material in the target 104 by an amount ε. The cross sections for scattering via the NRF state in the reference target 106 (acting as a reference scatterer) are shown at two different temperatures, each with a concomitantly different Doppler broadening. The sampling of different energy regions of the transmitted photon spectrum is apparent.

In another embodiment the temperature of the reference target 106 may also be varied to change the energy of the overlap region that the reference target 106 is sampling. This will provide information concerning the overlap region between the photon source 101 and the target 104, and provide a means of determining the Doppler broadening of the state of the material in the target 104. This approach is demonstrated in FIG. 9 where the intensity of the transmitted beam is displayed along with the cross section of a reference scatterer 106 at two temperatures illustrating the differing resonance overlaps at the two temperatures of the reference scatterer 106. The resonance energy of the reference target 106 is purposely displaced from the resonance energy of the material in the target 104 by an amount $\epsilon$ as defined above. This illustrates how the reference target 106 material may be of a different molecular structure than the material in the target 104 even though it contains the same nuclear isotope under study. By choosing molecules with different energies $\epsilon$, the position of the NRF state in the reference target 106 may be adjusted. This will assist in the use of a temperature variation to determine the broadening of the NRF state in the material in the target 104. Of course, the variation of $\epsilon$ is itself another way of scanning the broadening of the NRF state of the material in the target 104 and this represents another embodiment for this invention.

While the systems and methods disclosed herein have been particularly shown and described with references to exemplary embodiments thereof, it will be understood by those skilled in the art that various changes in form and details may be made therein without departing from the scope of the disclosure. It should be realized this invention is also capable of a wide variety of further and other embodiments within the spirit of the invention. Those skilled in the art will recognize or be able to ascertain using no more than routine experimentation, many equivalents to the exemplary embodiments described specifically herein. Such equivalents are intended to be encompassed in the scope of the present disclosure.

What is claimed is:

1. A method of obtaining information about a nuclear species of interest in a target, comprising:
   a) illuminating the target with photons from a photon source, wherein the photons upon impact have an energy spectrum of a predetermined central energy and a predetermined range that overlaps a nuclear resonance of the nuclear species of interest in the target;
   b) providing at least one photon detector to measure an intensity of photons scattered by nuclear resonance fluorescence from at least a portion of the target in at least one energy channel;
   c) repeating steps a)-b) at least one time, wherein upon each repetition the photons have an energy spectrum upon impact of a different at least one of a predetermined central energy and a predetermined range;
   d) based at least in part upon a measured intensity of photons scattered from the at least a portion of the target in at least one energy channel, determining at least one of an apparent width of the nuclear resonance in the nuclear species of interest in the target and an apparent shift of a central energy of the nuclear resonance in the nuclear species of interest in the target; and
   e) based upon at least one of the apparent width of the nuclear resonance and the apparent shift of the central energy of the nuclear resonance in the nuclear species of interest in the target, determining an identity of a molecule or a crystal containing the nuclear species of interest in the target.

2. The method of claim 1, further comprising determining a zero point momentum distribution of the nuclear species of interest in the target based at least in part upon the apparent width of the nuclear resonance.

3. The method of claim 1, further comprising determining the identity of the molecule or the crystal containing the nuclear species of interest in the target based at least in part upon the apparent width of the nuclear resonance.

4. The method of claim 1, further comprising determining the identity of the molecule or the crystal containing the nuclear species of interest in the target based at least in part upon the apparent shift of the central energy of the nuclear resonance.

5. The method of claim 1, wherein upon each repetition the photons have an energy spectrum upon impact of a different predetermined central energy.

6. The method of claim 5, wherein the energy spectrum upon impact of a different predetermined central energy is obtained by moving at least one of the photon source and the target relative to the other.

7. The method of claim 1, wherein upon each repetition the photons have an energy spectrum upon impact of a different predetermined range.

8. The method of claim 7, wherein the energy spectrum upon impact of a different predetermined range is obtained by heating the photon source.

9. A method of obtaining information about a nuclear species of interest in a target, comprising:
   a) illuminating the target with photons from a photon source, wherein the photons upon impact have an energy spectrum of a predetermined central energy and a predetermined range that overlaps a nuclear resonance of the nuclear species of interest in the target;
   b) providing at least one photon detector to measure an intensity of photons scattered by nuclear resonance fluorescence from at least a portion of the target in at least one energy channel;
   c) repeating steps a)-b) at least one time, wherein upon each repetition the target is heated to a different temperature;
   d) based at least in part upon a measured intensity of photons scattered from the at least a portion of the target in at least one energy channel, determining at least one of an apparent width of the nuclear resonance in the nuclear species of interest in the target and an apparent shift of a central energy of the nuclear resonance in the nuclear species of interest in the target; and
   e) based upon at least one of the apparent width of the nuclear resonance and the apparent shift of the central energy of the nuclear resonance in the nuclear species of interest in the target, determining an identity of a molecule or a crystal containing the nuclear species of interest in the target.

10. The method of claim 9, further comprising determining a zero point momentum distribution of the nuclear species of interest in the target based at least in part upon the apparent width of the nuclear resonance.

11. The method of claim 9, further comprising determining the identity of the molecule or the crystal containing the nuclear species of interest in the target based at least in part upon the apparent width of the nuclear resonance.

12. The method of claim 9, further comprising determining the identity of the molecule or the crystal containing the nuclear species of interest in the target based at least in part upon the apparent shift of the central energy of the nuclear resonance.

13. A method of obtaining information about a nuclear species of interest in a target, comprising:
   a) illuminating the target with photons from a photon source, wherein the photons have an energy spectrum upon impact of a predetermined central energy and a predetermined range that overlaps a nuclear resonance of the nuclear species of interest in the target;
   b) providing at least one reference scatterer, the reference scatterer comprising the nuclear species of interest;
   c) allowing photons transmitted through the target to scatter from the at least one reference scatterer;
   d) providing at least one photon detector to measure an intensity of photons scattered by nuclear resonance fluorescence from the at least one reference scatterer in at least one energy channel;
   e) repeating steps a)-d) at least one time, wherein upon each repetition the photons have an energy spectrum upon impact of a different at least one of a predetermined central energy and a predetermined range;
   f) based at least in part upon a measured intensity of photons scattered from the at least one reference scatterer in at least one energy channel, determining at least one of an apparent width of the nuclear resonance in the nuclear species of interest in the target and an apparent shift of a central energy of the nuclear resonance in the nuclear species of interest in the target; and
   g) based upon at least one of the apparent width of the nuclear resonance and the apparent shift of the central energy of the nuclear resonance in the nuclear species of interest in the target, determining an identity of a molecule or a crystal containing the nuclear species of interest in the target.

14. The method of claim 13, further comprising determining a zero point momentum distribution of the nuclear species of interest in the target based at least in part upon the apparent width of the nuclear resonance.

15. The method of claim 13, further comprising determining the identity of the molecule or the crystal containing the nuclear species of interest in the target based at least in part upon the apparent width of the nuclear resonance.

16. The method of claim 13, further comprising determining the identity of the molecule or the crystal containing the nuclear species of interest in the target based at least in part upon the apparent shift of the central energy of the nuclear resonance.

17. The method of claim 13, wherein upon each repetition the photons have an energy spectrum upon impact of a different predetermined central energy.

18. The method of claim 17, wherein the energy spectrum upon impact of a different predetermined central energy is obtained by moving at least one of the photon source and the target relative to the other.

19. The method of claim 13, wherein upon each repetition the photons have an energy spectrum upon impact of a different predetermined range.

20. The method of claim 19, wherein the energy spectrum upon impact of a different predetermined range is obtained by heating the photon source.

21. A method of obtaining information about a nuclear species of interest in a target, comprising:
   a) illuminating the target with photons from a photon source, wherein the photons upon impact have an energy spectrum of a predetermined central energy and a predetermined range that overlaps a nuclear resonance of the nuclear species of interest in the target;
   b) providing at least one reference scatterer, the reference scatterer comprising the nuclear species of interest;
   c) allowing photons transmitted through the target to scatter from the at least one reference scatterer;
   d) providing at least one photon detector to measure an intensity of photons scattered by nuclear resonance fluorescence from the at least one reference scatterer in at least one energy channel;
   e) repeating steps a)-d) at least one time, wherein upon each repetition the target is heated to a different temperature;
   f) based at least in part upon a measured intensity of photons scattered from the at least one reference scatterer in at least one energy channel, determining at least one of an apparent width of the nuclear resonance in the nuclear species of interest in the target and an apparent shift of a central energy of the nuclear resonance in the nuclear species of interest in the target; and
   g) based upon at least one of the apparent width of the nuclear resonance and the apparent shift of the central energy of the nuclear resonance in the nuclear species of interest in the target, determining an identity of a molecule or a crystal containing the nuclear species of interest in the target.

22. The method of claim 21, further comprising determining a zero point momentum distribution of the nuclear species of interest in the target based at least in part upon the apparent width of the nuclear resonance.

23. The method of claim 21, further comprising determining the identity of the molecule or the crystal containing the nuclear species of interest in the target based at least in part upon the apparent width of the nuclear resonance.

24. The method of claim 21, further comprising determining the identity of the molecule or the crystal containing the nuclear species of interest in the target based at least in part upon the apparent shift of the central energy of the nuclear resonance.

25. A method of obtaining information about a nuclear species of interest in a target, comprising:
   a) illuminating the target with photons from a photon source, wherein the photons have an energy spectrum upon impact of a predetermined central energy and a predetermined range that overlaps a nuclear resonance of the nuclear species of interest in the target;
   b) providing at least one photon detector to measure an intensity of photons scattered by nuclear resonance fluorescence from at least a portion of the target in at least one energy channel;
   c) providing at least one reference scatterer, the reference scatterer comprising at least one nuclear species of interest;
   d) allowing photons transmitted through the target to scatter from the at least one reference scatterer;
   e) providing at least one reference-photon detector to measure an intensity of photons scattered from the at least one reference scatterer in at least one reference-photon energy channel of interest;
   f) repeating steps a)-e) at least one time, wherein upon each repetition the photons have an energy spectrum upon impact of a different at least one of a predetermined central energy and a predetermined range;
   g) based at least in part upon a measured intensity of photons scattered from the at least a portion of the target in at least one energy channel, and upon a measured intensity of photons scattered from the at least one reference scatterer in at least one energy channel, determining at least one of an apparent width of the nuclear resonance in the nuclear species of interest in the target and an apparent shift of a central energy of the nuclear resonance in the nuclear species of interest in the target; and h) based upon at least one of the apparent width of the nuclear resonance and the apparent shift of the central energy of the nuclear resonance in the nuclear species of interest in the target, determining an identity of a molecule or a crystal containing the nuclear species of interest in the target.

26. The method of claim 25, further comprising determining a zero point momentum distribution of the nuclear species of interest in the target based at least in part upon the apparent width of the nuclear resonance.

27. The method of claim 25, further comprising determining the identity of the molecule or the crystal containing the nuclear species of interest in the target based at least in part upon the apparent width of the nuclear resonance.

28. The method of claim 25, further comprising determining the identity of the molecule or the crystal containing the nuclear species of interest in the target based at least in part upon the apparent shift of the central energy of the nuclear resonance.

29. The method of claim 25, wherein upon each repetition the photons have an energy spectrum upon impact of a different predetermined central energy.

30. The method of claim 29, wherein the energy spectrum upon impact of a different predetermined central energy is obtained by moving at least one of the photon source and the target relative to the other.

31. The method of claim 25, wherein upon each repetition the photons have an energy spectrum upon impact of a different predetermined range.

32. The method of claim 31, wherein the energy spectrum upon impact of a different predetermined range is obtained by heating the photon source.

33. A method of obtaining information about a nuclear species of interest in a target, comprising:
a) illuminating the target with photons from a photon source, wherein the photons upon impact have an energy spectrum of a predetermined central energy and a predetermined range that overlaps a nuclear resonance of the nuclear species of interest in the target;
b) providing at least one photon detector to measure an intensity of photons scattered by nuclear resonance fluorescence from at least a portion of the target in at least one energy channel;
c) providing at least one reference scatterer, the reference scatterer comprising at least one nuclear species of interest;
d) allowing photons transmitted through the target to scatter from the at least one reference scatterer;
e) providing at least one reference-photon detector to measure an intensity of photons scattered from the at least one reference scatterer in at least one reference-photon energy channel of interest;
f) repeating steps a)-e) at least one time, wherein upon each repetition the target is heated to a different temperature;
g) based at least in part upon a measured intensity of photons scattered from the at least a portion of the target in at least one energy channel, and upon a measured intensity of photons scattered from the at least one reference scatterer in at least one energy channel, determining at least one of an apparent width of the nuclear resonance in the nuclear species of interest in the target and an apparent shift of a central energy of the nuclear resonance in the nuclear species of interest in the target; and h) based upon at least one of the apparent width of the nuclear resonance and the apparent shift of the central energy of the nuclear resonance in the nuclear species of interest in the target, determining an identity of a molecule or a crystal containing the nuclear species of interest in the target.

34. The method of claim 33, further comprising determining a zero point momentum distribution of the nuclear species of interest in the target based at least in part upon the apparent width of the nuclear resonance.

35. The method of claim 33, further comprising determining the identity of the molecule or the crystal containing the nuclear species of interest in the target based at least in part upon the apparent width of the nuclear resonance.

36. The method of claim 33, further comprising determining the identity of the molecule or the crystal containing the nuclear species of interest in the target based at least in part upon the apparent shift of the central energy of the nuclear resonance.

37. A method of obtaining information about a nuclear species of interest in a target, comprising:
a) illuminating the target with photons from a photon source, wherein the photons have an energy spectrum upon impact of a predetermined central energy and a predetermined range that overlaps a nuclear resonance of the nuclear species of interest in the target;
b) providing at least one photon detector to measure an intensity of photons scattered by nuclear resonance fluorescence from at least a portion of the target in at least one energy channel;
c) providing at least one transmission detector;
d) allowing photons transmitted through the target to impact upon the at least one transmission detector;
e) repeating steps a)-d) at least one time, wherein upon each repetition the photons have an energy spectrum upon impact of a different at least one of a predetermined central energy and a predetermined range;
f) based upon a measured intensity of photons scattered from the at least a portion of the target in at least one energy channel, and upon a measured intensity of photons impacting upon the at least one transmission detector, determining at least one of an apparent width of the nuclear resonance in the nuclear species of interest in the target and an apparent shift of a central energy of the nuclear resonance in the nuclear species of interest in the target; and
g) based upon at least one of the apparent width of the nuclear resonance and the apparent shift of the central energy of the nuclear resonance in the nuclear species of interest in the target, determining an identity of a molecule or a crystal containing the nuclear species of interest in the target.

38. The method of claim 37, further comprising determining a zero point momentum distribution of the nuclear species of interest in the target based at least in part upon the apparent width of the nuclear resonance.

39. The method of claim 37, further comprising determining determining the identity of the molecule or the crystal containing the nuclear species of interest in the target based at least in part upon the apparent width of the nuclear resonance.

40. The method of claim 37, further comprising determining the identity of the molecule or the crystal containing the nuclear species of interest in the target based at least in part upon the apparent shift of the central energy of the nuclear resonance.

41. The method of claim 37, wherein upon each repetition the photons have an energy spectrum upon impact of a different predetermined central energy.

42. The method of claim 41, wherein the energy spectrum upon impact of a different predetermined central energy is obtained by moving at least one of the photon source and the target relative to the other.

43. The method of claim 37, wherein upon each repetition the photons have an energy spectrum upon impact of a different predetermined range.

44. The method of claim 43, wherein the energy spectrum upon impact of a different predetermined range is obtained by heating the photon source.

45. A method of obtaining information about a nuclear species of interest in a target, comprising:
   a) illuminating the target with photons from a photon source, wherein the photons upon impact have an energy spectrum of a predetermined central energy and a predetermined range that overlaps a nuclear resonance of the nuclear species of interest in the target;
   b) providing at least one photon detector to measure an intensity of photons scattered by nuclear resonance fluorescence from at least a portion of the target in at least one energy channel;
   c) providing at least one transmission detector;
   d) allowing photons transmitted through the target to impact upon the at least one transmission detector;
   e) repeating steps a)-d) at least one time, wherein upon each repetition the target is heated to a different temperature;
   f) based upon a measured intensity of photons scattered from the at least a portion of the target in at least one energy channel, and upon a measured intensity of photons impacting upon the at least one transmission detector, determining at least one of an apparent width of the nuclear resonance in the nuclear species of interest in the target and an apparent shift of a central energy of the nuclear resonance in the nuclear species of interest in the target; and
   g) based upon at least one of the apparent width of the nuclear resonance and the apparent shift of the central energy of the nuclear resonance in the nuclear species of interest in the target, determining an identity of a molecule or a crystal containing the nuclear species of interest in the target.

46. The method of claim 45, further comprising determining a zero point momentum distribution of the nuclear species of interest in the target based at least in part upon the apparent width of the nuclear resonance.

47. The method of claim 45, further comprising determining the identity of the molecule or the crystal containing the nuclear species of interest in the target based at least in part upon the apparent width of the nuclear resonance.

48. The method of claim 45, further comprising determining the identity of the molecule or the crystal containing the nuclear species of interest in the target based at least in part upon the apparent shift of the central energy of the nuclear resonance.

* * * * *